United States Patent
McComber et al.

(10) Patent No.: US 11,957,502 B2
(45) Date of Patent: Apr. 16, 2024

(54) EXPOSURE CONTROL BASED ON DETECTOR MOVEMENT

(71) Applicant: CARESTREAM HEALTH, INC., Rochester, NY (US)

(72) Inventors: Brandon McComber, Webster, NY (US); Brian M. Colwell, Rochester, NY (US); Damon Wilkins, Avon, NY (US); Scott Warner, Ontario, NY (US)

(73) Assignee: Carestream Health, Inc., Rochester, NY (US)

( * ) Notice: Subject to any disclaimer, the term of this patent is extended or adjusted under 35 U.S.C. 154(b) by 374 days.

(21) Appl. No.: 17/548,742

(22) Filed: Dec. 13, 2021

(65) Prior Publication Data

US 2022/0183651 A1 Jun. 16, 2022

Related U.S. Application Data

(60) Provisional application No. 63/126,160, filed on Dec. 16, 2020.

(51) Int. Cl.
*A61B 6/00* (2006.01)
*A61B 6/42* (2024.01)

(52) U.S. Cl.
CPC ............ *A61B 6/547* (2013.01); *A61B 6/4266* (2013.01); *A61B 6/56* (2013.01)

(58) Field of Classification Search
CPC ......... A61B 6/4266; A61B 6/547; A61B 6/56; A61B 6/4283; A61B 6/4405; A61B 6/4452; A61B 6/54
See application file for complete search history.

(56) References Cited

U.S. PATENT DOCUMENTS

2013/0188856 A1* 7/2013 Adler, Jr. ............... A61B 6/463
382/132

* cited by examiner

*Primary Examiner* — Dani Fox

(57) ABSTRACT

A radiographic imaging system having a number of useable digital radiographic detectors selectively activates one of the detectors to capture a radiographic image. The DR detectors each include a movement detector configured to transmit a movement signal when a movement of the corresponding detector is sensed. A portion of the system is disabled in response to receiving a movement signal transmitted from a motion sensor in a detector other than the active detector.

9 Claims, 3 Drawing Sheets

EXPOSURE CONTROL BASED ON DETECTOR MOVEMENT

This application claims priority to U.S. Patent Application Ser. No. 63/126,160, filed Dec. 16, 2020, in the name of McComber et al., and entitled X-RAY EXPOSURE CONTROL BASED ON DETECTOR MOVEMENT, which is hereby incorporated by reference herein in its entirety.

BACKGROUND OF THE INVENTION

The subject matter disclosed herein relates to operator use of digital radiographic detectors for x-ray exposures. The present invention applies to medical digital x-ray imaging. Included modalities are conventional 2-dimensional radiography with computed radiography (CR) cassettes and digital flat panel detectors, long length imaging, any form of computed tomography including cone beam computed tomography (CBCT), tomosynthesis, and fluoroscopy.

It is common practice to have multiple x-ray detectors enabled, such as being powered on and ready for image capture, when preparing for an x-ray examination in order to support capturing a range of x-ray image sizes and providing a range of image quality capabilities. However, only one "active" detector can be set to receive the x-ray beam and create a resultant image. This is typically implemented by registering with the radiographic, imaging system an identifier distinguishing one detector to be programmably linked as the active detector. Sometimes, a technologist has to swap out the active detector with a different detector due to various events: e.g., the patient is too large and/or small and so requires a different size detector, the active detector was soiled, the technologist is distracted by answering patient questions and accidentally picks up the wrong, non-active detector. If the technologist positions a non-active detector for use and exposes a patient, no image will be acquired and the patient will have been needlessly exposed to X-ray radiation.

The discussion above is merely provided for general background information and is not intended to be used as an aid in determining the scope of the claimed subject matter.

BRIEF DESCRIPTION OF THE INVENTION

A radiographic imaging system having a number of useable digital radiographic detectors selectively digitally registers (makes active) one of the detectors to be used to capture a radiographic image. The DR detectors each include a movement sensor configured to transmit a movement signal when a movement of the corresponding detector is sensed. A portion of the system is disabled in response to receiving a movement signal transmitted from a sensor in a detector other than the active detector. An advantage that may be realized in the practice of some disclosed embodiments is prevention of patient exposure to unnecessary ionizing radiation.

In one embodiment, a radiographic imaging system includes an x-ray source and a number of digital radiographic detectors each having a motion sensor configured to transmit a movement signal when the detector is moved. The imaging system designates one of the plurality of DR detectors as an active detector and disables activation of the x-ray source in response to receiving a movement signal transmitted from a detector other than the active detector.

In one embodiment, a method includes providing a plurality of DR detectors for use with an x-ray imaging system. The DR detectors each have a corresponding motion sensor that transmits a movement signal when the motion sensor is moved. Only one of the DR detectors is designated as an active detector and the imaging system is disabled when a movement signal is received from a motion sensor in a detector that is not designated as the active detector.

In one embodiment, a radiographic imaging system includes a number of digital radiographic detectors each having a motion sensor configured to transmit a movement signal when it is moved. The imaging system designates only one of the DR detectors as an active detector, and disables activation of at least a portion of the imaging system in response to receiving a movement signal transmitted from a motion sensor corresponding to a detector other than the active detector.

This invention uses a motion sensor signal as a trigger to inform the technologist when a non-active detector has been moved, which may indicate that the technologist has moved the non-active detector such as by mistakenly placing it behind a patient with the intention of using it. The x-ray imaging system, having a central processing system, may be configured to disable exposures when the system receives a movement signal from a non-active detector until the technologist confirms that the active detector is being used.

All enabled detectors report their states to the radiographic imaging system periodically. The detectors each include a motion sensor, such as an accelerometer, which detects movement of the detector. Thus, when movement is sensed by a motion sensor, the detector sends a signal to the imaging system indicating that the corresponding detector has moved. The system uses an electronically stored list of enabled detectors along with a designation of the active detector intended for use in the x-ray imaging procedure. The active detector may be designated by the technologist, who inputs a selection, or it may be selected by the imaging system automatically. The imaging system is programmed to ignore signals indicating motion of the active detector, but will automatically shut down exposure capability of the imaging system if motion is sensed from a non-active detector.

The imaging system may automatically set itself into an exposure control state when an x-ray examination set-up procedure begins. The set-up procedure may be initiated by a technologist or may be automatically started by the x-ray imaging system when the system detects that a technologist is accessing a patient record, manipulates the tube head out of a docked position, begins setting power levels for an exposure, or selects a detector as the active detector, for example. When the imaging system is in the exposure control state, movement of non-active detectors, as explained above, will trigger the imaging system to disable the imaging system's exposure capability and to notify an operator, such as by displaying a message on the imaging system display, indicating its disabled state. The imaging system will require that the technologist enter a confirmation that the active detector is being used for the current x-ray examination in order to reenable the imaging system.

The summary descriptions above are not meant to describe individual separate embodiments whose elements are not interchangeable. In fact, many of the elements described as related to a particular embodiment can be, used together with, and possibly interchanged with, elements of other described embodiments. Many changes and modifications may be made within the scope of the present invention without departing from the spirit thereof, and the invention includes all such modifications.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings below are intended to be drawn neither to any precise scale with respect to relative size, angular relationship, relative position, or timing relationship, nor to any combinational relationship with respect to interchangeability, substitution, or representation of a required implementation, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

Figure 1:
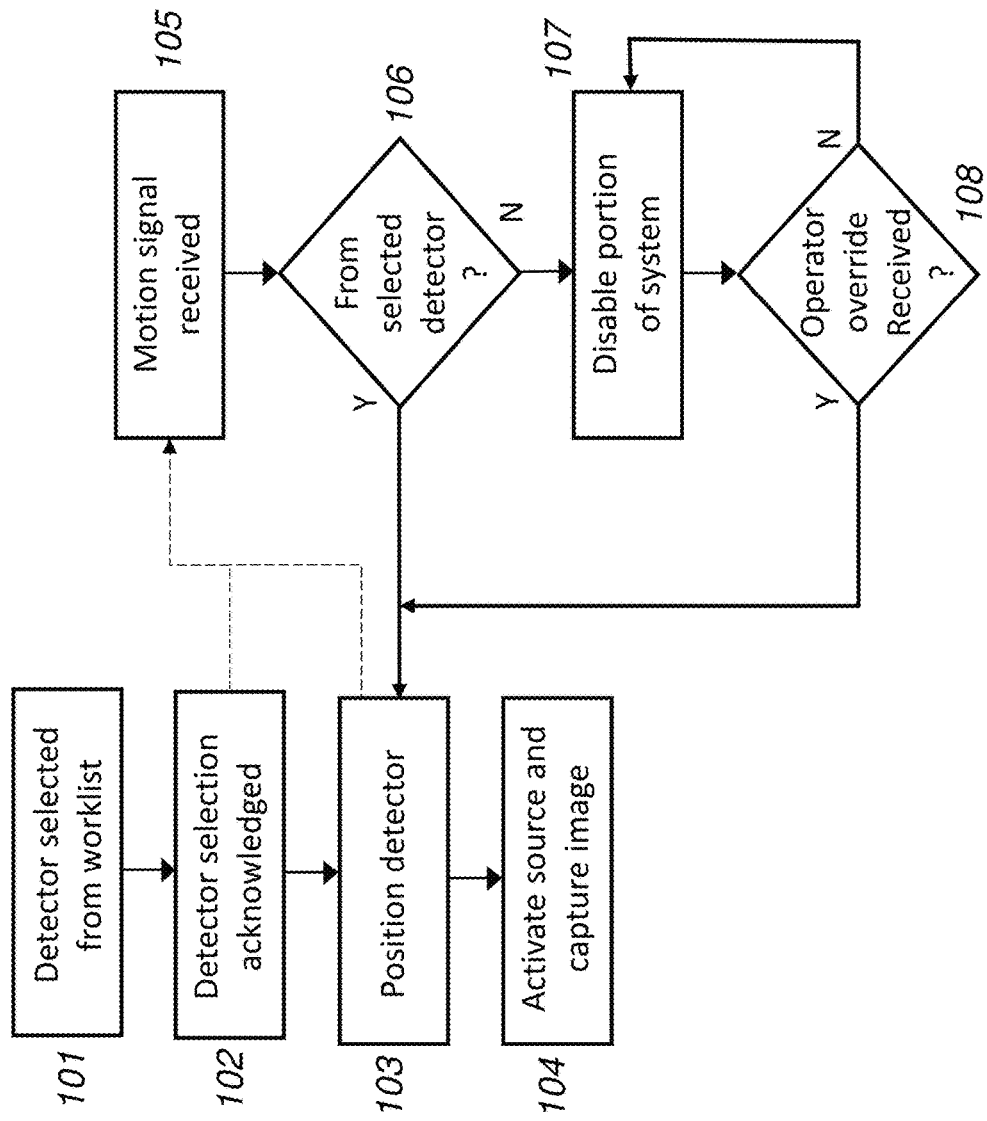
FIG. 1 is a flow diagram for practicing an embodiment of the present invention.

The flow diagram of FIG. 1 illustrates steps of operating a radiographic imaging system that is programmed according to embodiments disclosed herein. In step 101 an operator selects a digital radiographic (DR) detector from a list of available DR detectors to be used for radiographically imaging a subject. The selection step 101 may be performed by an operator using an input device that is part of the radiographic imaging system, such as a keyboard or a graphical user interface (GUI) presented to the operator on a display screen. An operator may navigate through a list of available detectors displayed on the GUI, each associated with a unique displayed identifier, using a mouse or keyboard and thereby input a selection that is detected and acknowledged by the imaging system. In one embodiment the GUI may be presented on a touch screen and the operator may make a selection by manually touching the screen. After the operator makes a DR detector selection, the radiographic imaging system acknowledges that the selection is received, in step 102, which includes verifying that the selected DR detector is in electronic communication, or linked with the radiographic imaging system via a connected cable, or wirelessly via radio frequency communication. The selected DR detector identifier is recorded by the radiographic imaging system. At step 103, the operator positions the DR detector at an appropriate location relative to a subject being imaged, and positions a radiographic energy source, such as an x-ray source, aimed at the subject and the selected DR detector. At step 104 the operator activates the radiographic energy source, such as an x-ray source, such that the DR detector captures a radiographic image of the subject. The steps 101-104 described thus far may be considered standard practice as used in typical radiographic imaging procedures.

As disclosed herein, the present invention makes use of motion sensors that are disposed in or on DR detectors that may be used together with a radiographic imaging system. Such motion sensors may detect motion and, in response to such detection, transmit a notification signal to the detector in which the motion sensor is disposed. The detector transmits a motion signal together with a detector identifier to the radiographic imaging system whenever a notification signal is transmitted by the motion sensor. Referring to FIG. 1, at some point in time after step 101 and before step 104, a motion signal transmitted by a DR detector may be received at the radiographic imaging system, at step 105. In response to receiving the motion signal and DR detector identifier, the radiographic imaging system may determine, at step 106, whether the motion signal was transmitted by the DR detector that was selected in step 101 and acknowledged in step 102. In one embodiment, this determination may be made by the radiographic, imaging system by comparing the identifier recorded in response to the operator selection in step 101 to the identifier received with the transmitted motion signal. If the comparison indicates that the identifiers match, then, at step 106, the radiographic imaging system takes no action in response and allows the operator to continue with the imaging procedure, such as by positioning the selected detector as in step 103. If, at step 106, the radiographic imaging system determines that the motion signal is received from a DR detector having an identifier that is different from the identifier of the operator selected DR detector, the radiographic imaging system will disable a portion of the system at step 107. For example, the radiographic imaging system may disable the x-ray source to prevent its activation, and indicate the disabled state using an audible or visual signal device, or both. In response to the disable signal, an operator may override the disablement by entering an override instruction to the radiographic imaging system at step 108 whereby the radiographic imaging system enables any disabled portions of the radiographic imaging system and allows the operator to continue the imaging procedure. Before entering an override instruction, the operator may verify that the motion signal was caused by an extraneous movement of an unselected DR detector and that the selected DR detector is, in fact, being prepared for imaging the subject.

Figure 2:
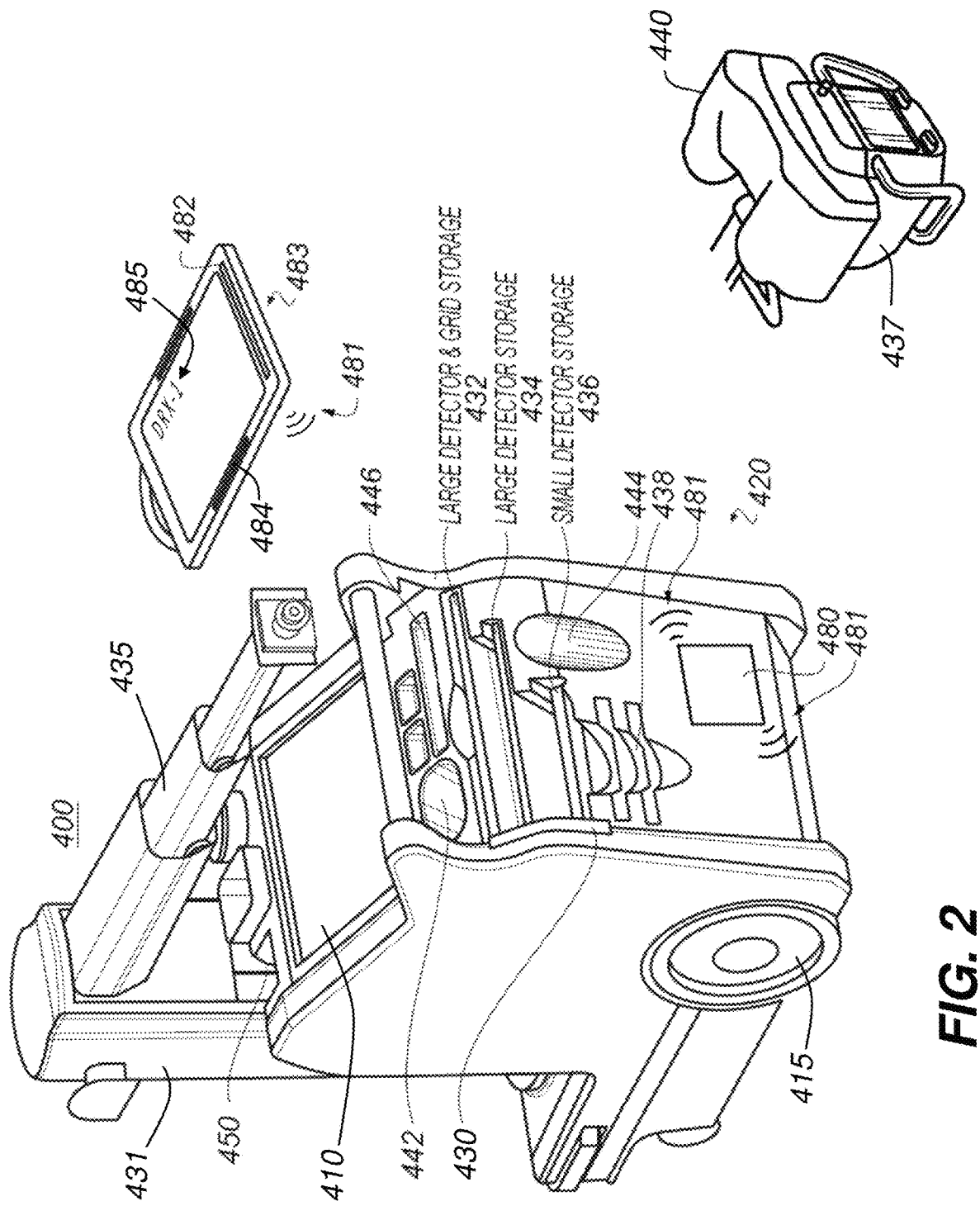
FIG. 2 is a perspective view of a mobile radiographic system that implements the present invention.

FIG. 2 is a perspective view of an exemplary mobile radiography system 400 wherein the present invention may be implemented. The exemplary mobile x-ray or radiography system 400 may be employed using computed radiography (CR) cassettes and/or digital flat panel detectors. As shown in FIG. 2, the mobile radiography system 400 may include a moveable transport frame 420 that includes a digital display 410, or digital monitor, electronically connected to the central processing system 480. The display 410 may be used to display relevant information such as captured radiographic images, related data such as alphanumeric information and status of the radiography apparatus, such as activation ready, disabled, or other system status information. The display 410 may implement or display input controls (e.g., touch screen GUI) to communicate instructions to the central processing system 480 to initiate functions to operate the mobile radiography system 400, such as initiating, generating, storing, transmitting, modifying, and printing of any captured image(s) and may include an integral or separate control panel (not shown) to assist in setting up exposure parameters such as x-ray source power levels.

For mobility, the mobile radiographic system 400 may include one or more wheels 415 that allows an operator to roll the mobile radiographic system 400 over a surface such as a floor to a desired location. A self-contained battery pack (e.g., rechargeable) may provide source power, which may reduce or eliminate the need for operation near a power outlet. The on-board self-contained battery pack can provide power to the central processing system 480.

Mounted to the transport frame 420 is a support structure including a vertical support column 431 and horizontal boom 435, coupled to the frame 420 and providing a structure that supports the tube head 440 which includes an x-ray source therewithin and a collimator 437. The tube head 440 is shown detached from the horizontal boom 435 for clarity of illustration. The mobile radiographic system 400 may include a storage area 430 disposed in the transport frame that can include a plurality of individual bins or slots for removably storing DR detectors or CR cassettes, such as large detector and grid storage 432, large detector storage 434, and/or small detector storage 436, 438, that each may hold a detector inserted therein. Additional storage areas at the mobile radiography system 400 can include storage 442, 444, 446, 450 for other devices.

As shown in FIG. 2, the mobile radiography system 400 may be configured with a central processing system 480 capable of wireless communication to transmit and receive signals 481 to/from various digital devices such as x-ray detectors 432, 434, 436, 438, 483, each provided with a processor 482 configured to enable receiving and transmitting radio frequency (RF) signals with mobile radiography system 400. The processors 482, such as in the digital detector 483, are configured to receive a notification signal from an on-board motion sensor 484, such as an accelerometer, when the motion sensor 484 detects that it has moved, i.e., movement of its corresponding detector 483. The DR detectors 432, 434, 436, 438, 483, may each display a unique identifier 485 on a surface thereof. The DR detectors 432, 434, 436, 438, 483, may include wireless transceivers therein for transmitting radio frequency signals 481 such as instructions, commands, and/or requests to a processing system 480 of the mobile radiography system 400.

According to an embodiment of the present disclosure, a number of selectable digital detectors 432, 434, 436, 438, 483 are each stored in a corresponding storage bin in the moveable transport frame of mobile radiographic system 400. Each of the digital detectors 432, 434, 436, 438, 483, is configured to capture a radiographic image generated by x-rays from the x-ray source in tube head 440.

Figure 3:
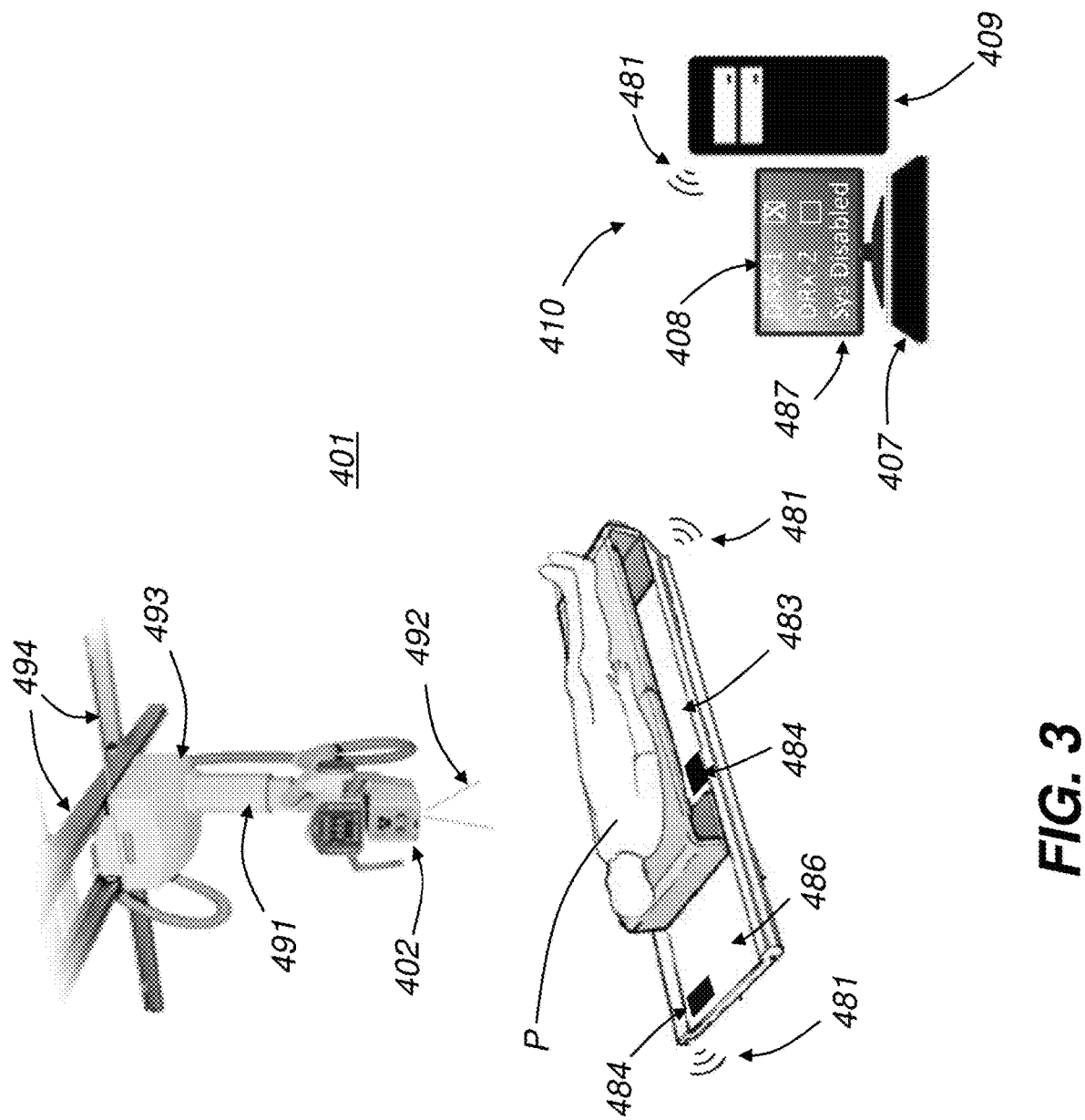
FIG. 3 is a perspective view of a stationary radiographic system that implements the present invention.

With reference to the flow diagram of FIG. 1, the mobile radiography system 400 may be programmed with software instructions stored in processing system 480 for controlling operation of the mobile radiography system 400 accordingly. An operator may select a digital radiographic (DR) detector from a list of available DR detectors displayed on display screen 410 (see e.g., FIG. 3 display) to be used for radiographically imaging a subject. The displayed list of selectable detectors may correspond to the detectors 432, 434, 436, 438, 483. The selection may be performed by an operator using an input device (not shown) that is part of the radiographic imaging system. In one embodiment a GUI may be presented on display 410, which may be a touch screen display, and the operator may make a selection by manually touching the display 410. After the operator makes a DR detector selection, the radiographic imaging system 400 may acknowledge the selection such as displaying an "X" next to the selected DR detector identifier (FIG. 3). The selected DR detector 483 is recorded by the radiographic imaging system 400 according to a detector identifier, such as DRX-1, for example. The operator may then proceed to position the selected DR detector 483 at an appropriate location relative to a subject being imaged, and position the tube head 440 such that the x-ray source is aimed at both a subject to be imaged and the selected DR detector 483. The operator may then activate the x-ray source in tube head 440 such that the selected DR detector 483 captures a radiographic image of the subject.

After the operator has selected a detector using the display 410 as described above, the radiography system 400 may receive a motion signal transmitted from any of detectors 432, 434, 436, 438, 483, together with a corresponding detector identifier. In response to receiving the motion signal and DR detector identifier, the radiographic imaging system 400 determines whether the motion signal was transmitted by the selected DR detector 483 identified as DRX-1. If the radiography system 400 determines that the motion signal was transmitted from the detector 483 corresponding to identifier DRX-1 the radiographic imaging system 400 takes no further responsive action and the operator may proceed with the imaging procedure. If the radiographic imaging system determines, based on a logical comparison, that the motion signal is received from a non-selected, non-active DR detector 432, 434, 436, 438, having an identifier, e.g. DRX-2, that is different from the identifier, e.g., DRX-1, of the operator selected DR detector 483, the radiographic imaging system 400 will disable a portion of the radiography system 400, such as disabling the x-ray source in tube head 440, to prevent its activation. The radiography system 400 may indicate the disabled state audibly using a speaker (not shown) or visually by displaying a disable message or signal on the display 410. If the x-ray source is disabled, an operator may override the disablement by entering an override instruction via the display 410 to the radiographic imaging system 400, whereby the radiographic imaging system reenables any disabled portions of the radiographic imaging system 400, thereby allowing the operator to continue preparing for an x-ray imaging exam. Before entering an override instruction, operator may verify that the received motion signal was caused by an unintentional or extraneous movement of an unselected DR detector 432, 434, 436, 438, and that the selected DR detector 483 is, in fact, being prepared for use in the imaging exam. This programmed system procedure insures that the operator has not removed an unselected detector 432, 434, 436, 438, from the storage area 430 with the intention of positioning it for an x-ray exam, because movement of the unselected detector 432, 434, 436, 438, will result in a system disablement that will not allow the operator to expose a subject to x-rays until the operator verifies that the selected, acknowledged detector 483 is being prepared for imaging.

FIG. 3 is a perspective view of an exemplary stationary radiography system 401 wherein the present invention may be implemented. The exemplary stationary radiography system 401 may be employed using computed radiography (CR) cassettes and/or digital flat panel detectors. As shown in FIG. 3, the stationary radiography system 401 may include a motorized transport frame 493 that may be controllably moved in different directions along transverse rails 494 mounted on a ceiling. A processing system console 410 is electronically coupled to the motorized transport frame 493 and the tube head 402 for controlling movement of the tube head 402 and operation of the stationary radiography system 401. Processing system console 410 includes a digital display 408, or digital monitor, to display relevant information such as captured radiographic images, related data such as alphanumeric information and status of the stationary radiography system 401, such as activation ready, disabled, or other system status information. The display 408 may implement or display input controls (e.g., a touch screen) to communicate instructions to the processing system console 410 to initiate functions to operate the stationary radiography system 401, such as initiating, generating, storing, transmitting, modifying, and printing of any captured image(s) and may include an integral or separate control panel, such as keyboard 407 to assist in setting up exposure parameters such as x-ray source power levels. The console processing system 410 may include a CPU with electronic storage 409 including software programs for implementing the invention as described herein.

Mounted to the motorized transport frame 493 is a support structure including a telescoping vertical support column 491 that is extendable and retractable along a vertical axis. The vertical support column 491 has attached at one end thereto a tube head 402, which includes an x-ray source therewithin. The stationary radiographic system 401 may be moved into position over a subject, such as patient P, supported on bed having a detector 483 positioned underneath the subject P for capturing images of the subject P exposed by x-rays 492 from an x-ray source in tube had 402. Another detector 486 may also be available to the system 401 for capturing images of the subject P as needed. The central processing console 410 may be capable of wired or wireless communication to transmit and receive signals 481 to and from various digital devices such as the x-ray detector 483 positioned under subject P. Electronics contained in detectors 483, 486, may include a motion sensor 484, such as an accelerometer, as described herein. The available DR detectors 483, 486, may be displayed according to their identifiers, e.g., DRX-1 and DRX-2, on the display screen 408. The DR detectors 483, 486, may also include wireless transceivers therein for wirelessly transmitting signals 481 such as instructions, commands, and/or requests to console processing system 410. According to an embodiment of the present disclosure, the selectable digital detectors 483, 486, are each is configured to capture a radiographic image of a subject P using x-rays 492 generated from the x-ray source in tube head 402.

With reference to the flow diagram of FIG. 1, the stationary radiography system 401 controlled by local or remote central processing console 410 may be programmed with software instructions stored at processing console 410 for controlling operation of the stationary radiography system 401 accordingly. An operator may select a digital radiographic (DR) detector identifier from a list of available DR detector identifiers, DRX-1, DRX-2, corresponding to detectors 483, 486, respectively, displayed on display screen 408 to be used for radiographically imaging a subject, such as a patient P. The selection may be performed by an operator using an input device, such as keyboard 407, that is operatively part of the stationary radiographic imaging system 401. In one embodiment a GUI may be presented on display 408, which may be a touch screen display, and the operator may make a selection by manually touching the display 408 or entering a selection via keyboard 407. After the operator makes a DR detector selection, the stationary radiographic imaging system 401 may acknowledge the selection such as displaying an "X" next to the selected DR detector identifier, as shown on display 408. The selected DR detector is recorded by the central processing console 410 of the stationary radiographic imaging system 401 according to the detector identifier, DRX-1. The operator may then proceed to position the selected DR detector 483 at an appropriate location relative to a subject P being imaged, and position the tube head 402 such that the x-ray source therewithin is aimed at both the subject to be imaged P and the selected DR detector 483. The operator may then activate the x-ray source in tube head 402 such that the selected DR detector 483 captures a radiographic image of the subject P.

After the operator has selected a detector using the display 408 as described above, the radiography system 401 may detect a motion signal transmitted from a detector 484, and a corresponding detector identifier DRX-2. In response to receiving the motion signal and DR detector identifier, the console control system 410 determines whether the motion signal was transmitted by the selected DR detector 483, such as by comparing the recorded, selected identifier, DRX-1, with the identifier transmitted with the motion signal. If the radiography system 410 determines that the motion signal was transmitted from the selected, active detector 483, the radiographic imaging system 410 takes no action in response and the operator proceeds with the procedure for imaging subject P. If the radiographic imaging system 410 determines that the motion signal is received from the DR detector 484 having an identifier DRX-2 different from the operator selected DR detector 483, the radiographic imaging system 410 will disable a portion of the radiography system 401, such as disabling the x-ray source in tube head 402 to prevent its activation. The radiography system 401 may indicate the disabled state audibly using a speaker (not shown) or visually by displaying a disable message 487 or signal on the display 408. If the x-ray source in tube head 402 is disabled, an operator may override the disablement by entering an override instruction via the display 408 or keyboard 407 to the radiographic imaging system 401, whereby the radiographic imaging system reenables any disabled portions of the radiographic imaging system 401, thereby allowing the operator to continue preparing for an x-ray imaging exam of subject P. Before entering an override instruction, the operator may verify that the motion signal was caused by an unintentional or extraneous movement of the DR detector 484 and that the selected DR detector 483, or DRX-1 is, in fact, being prepared for use to image subject P. This programmed system procedure insures that the operator has not moved an unselected detector with the intention of positioning it for an x-ray exam of subject P. An unselected detector that is moved into an imaging position relative to a subject P will not respond to synchronization and image capture timing signals transmitted from imaging system 401, which may result in the need to repeat the imaging exam as no image will be captured in the unselected detector. In view of the foregoing, embodiments of the invention help to prevent of patient exposure to unnecessary ionizing radiation.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.), or an embodiment combining software and hardware aspects that may all generally be referred to herein as a "service," "circuit," "circuitry," "module," and/or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Program code and/or executable instructions embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer (device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

This description of the invention is intended to provide an overview of subject matter disclosed herein according to one or more illustrative embodiments. This description is provided to introduce an illustrative selection of embodiments. This description is intended to identify selected features of the subject matter. The subject matter is not limited to implementations that solve any or all disadvantages noted. So that the manner in which the features of the invention can be understood, a description of the invention may be had by reference to certain embodiments, some of which are illustrated in the accompanying drawings. It is to be noted, however, that the drawings illustrate certain embodiments of this invention and are therefore not to be considered limiting of its scope, for the scope of the invention encompasses other equally effective embodiments. As will be appreciated by one skilled in the art, aspects of the present invention may be embodied as a system, method, or computer program product.

What is claimed is:

1. A radiographic imaging system comprising:
an x-ray source; and
a plurality of digital radiographic detectors, the plurality of DR detectors each comprising a motion sensor, each motion sensor configured to transmit a movement signal when a corresponding detector is moved,
wherein the imaging system is configured to designate one of the plurality of DR detectors as an active detector, and wherein the imaging system is further configured to disable activation of the x-ray source in response to the imaging system receiving a movement signal transmitted from a motion sensor corresponding to a detector other than the active detector.

2. The system of claim 1, wherein the imaging system is further configured to ignore a movement signal transmitted from a motion sensor corresponding to the active detector.

3. The system of claim 1, wherein the imaging system is further configured to reenable activation of the x-ray source, after activation of the x-ray source is disabled by the imaging system, in response to receiving an operator input requesting that the x-ray source be reenabled.

4. A method of operating an x-ray imaging system, the method comprising:
- providing a plurality of DR detectors for use with the x-ray imaging system, the plurality of DR detectors each having a corresponding motion sensor that transmits a movement signal when the motion sensor is moved;
- designating only one of the plurality of DR detectors as an active detector; and
- disabling the imaging system when a movement signal is received from a motion sensor corresponding to a detector that is not designated as the active detector.

5. The method of claim 4, further comprising the imaging system ignoring a movement signal transmitted from a motion sensor corresponding to the designated active detector.

6. The method of claim 4, further comprising reenabling the imaging system, after the imaging system is disabled, in response to receiving an operator input requesting that the imaging system be reenabled.

7. A radiographic imaging system comprising:
- a plurality of digital radiographic detectors, the plurality of DR detectors each comprising a motion sensor, each motion sensor configured to transmit a movement signal when a corresponding detector is moved,
- wherein the imaging system is configured to designate only one of the plurality of DR detectors as an active detector, and wherein the imaging system is further configured to disable activation of at least a portion of the in aging system in response to the imaging system receiving a movement signal transmitted from a motion sensor corresponding to a detector other than the active detector.

8. The system of claim 7, wherein the imaging system is further configured to ignore a movement signal transmitted from a motion sensor corresponding to the active detector.

9. The system of claim 7, wherein the imaging system is further configured to reenable said at least a portion of the imaging system, after said at least a portion of the imaging system is disabled, in response to receiving an operator input requesting that said at least a portion of the imaging system be reenabled.

* * * * *

UNITED STATES PATENT AND TRADEMARK OFFICE
CERTIFICATE OF CORRECTION

| | | |
|---|---|---|
| PATENT NO. | : 11,957,502 B2 | Page 1 of 1 |
| APPLICATION NO. | : 17/548742 | |
| DATED | : April 16, 2024 | |
| INVENTOR(S) | : McComber et al. | |

It is certified that error appears in the above-identified patent and that said Letters Patent is hereby corrected as shown below:

In the Claims

Column 12, Claim 7, Line 10    Please replace "the in aging system in response to the imaging system" with --the imaging system in response to the imaging system--

Signed and Sealed this
Fourth Day of June, 2024

Katherine Kelly Vidal
*Director of the United States Patent and Trademark Office*